US009844234B2

(12) United States Patent
Thorens et al.

(10) Patent No.: US 9,844,234 B2
(45) Date of Patent: Dec. 19, 2017

(54) AEROSOL GENERATING SYSTEM WITH LEAKAGE PREVENTION

(75) Inventors: Michel Thorens, Moudon (CH); Jean-Marc Flick, Pomy (CH); Olivier Yves Cochand, Dombresson (CH); Flavien Dubief, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 645 days.

(21) Appl. No.: 13/990,080

(22) PCT Filed: Dec. 1, 2011

(86) PCT No.: PCT/EP2011/071553
§ 371 (c)(1),
(2), (4) Date: Aug. 6, 2013

(87) PCT Pub. No.: WO2012/072762
PCT Pub. Date: Jun. 7, 2012

(65) Prior Publication Data
US 2013/0306065 A1    Nov. 21, 2013

(30) Foreign Application Priority Data

Dec. 3, 2010    (EP) .................................... 10252050

(51) Int. Cl.
*A24F 47/00*    (2006.01)
*A61M 15/06*    (2006.01)

(52) U.S. Cl.
CPC .......... *A24F 47/008* (2013.01); *A24F 47/002* (2013.01); *A61M 15/06* (2013.01)

(58) Field of Classification Search
CPC .... A24F 47/008; A24F 47/002; A24B 15/165; A24B 15/18; A61M 16/108;
(Continued)

(56) References Cited

U.S. PATENT DOCUMENTS

| 4,284,089 A * | 8/1981 | Ray ...................... A24F 47/002 |
| | | 128/202.21 |
| 2009/0272379 A1* | 11/2009 | Thorens ................... A24D 3/18 |
| | | 128/202.21 |

(Continued)

FOREIGN PATENT DOCUMENTS

| CN | 1205849 A | 1/1999 |
| CN | 200983833 Y | 12/2007 |

(Continued)

OTHER PUBLICATIONS

Office Action dated Jul. 30, 2014 in Colombian Patent Application No. 13156661 (with English language translation).

(Continued)

*Primary Examiner* — Todd J Scherbel
*Assistant Examiner* — Elliot S Ruddie
(74) *Attorney, Agent, or Firm* — Oblon, McClelland, Maier & Neustadt, L.L.P.

(57) ABSTRACT

There is provided an aerosol generating system for heating a liquid aerosol-forming substrate. The system includes a liquid storage portion for storing the liquid aerosol-forming substrate, and a leakage preventer for preventing or reducing leakage of the liquid aerosol forming substrate from the liquid storage portion. The leakage preventer may include one or more of a porous plug at least partially located within the liquid storage portion, a first sealer between the liquid storage portion and a capillary wick, and a second sealer between the liquid storage portion and an electrical connector of an electric heater.

11 Claims, 3 Drawing Sheets

(58) Field of Classification Search
CPC .. A61M 16/202; A61M 11/041; A61M 15/06; A61M 16/0808; A61M 2016/0024; A61M 2205/3646
USPC .......................... 128/202.21, 203.26; 290/1 R
See application file for complete search history.

(56) References Cited

U.S. PATENT DOCUMENTS

| | | | |
|---|---|---|---|
| 2010/0242974 A1 | 9/2010 | Pan | |
| 2011/0011396 A1 | 1/2011 | Fang | |
| 2011/0303231 A1* | 12/2011 | Li | A24F 47/008 131/329 |

FOREIGN PATENT DOCUMENTS

| | | |
|---|---|---|
| CN | 201277443 Y | 7/2009 |
| CN | 101518361 A | 9/2009 |
| CN | 101606758 | 12/2009 |
| CN | 201547768 U | 8/2010 |
| CN | 101843368 A | 9/2010 |
| GB | 2468932 | 9/2010 |
| JP | 7-30677 U | 6/1995 |
| JP | 2009-537119 A | 10/2009 |
| KR | 10-2009-0122159 A | 11/2009 |
| WO | 2009132793 | 11/2009 |

OTHER PUBLICATIONS

International Search Report and Written Opinion dated Mar. 6, 2012 in International Application No. PCT/EP2011/071553.
Combined Chinese Office Action and Search Report dated Dec. 18, 2014 in Patent Application No. 201180058213.4 (with partial English language translation).
Combined Office Action and Search Report dated Aug. 13, 2015 in Chinese Patent Application No. 201180058213.4 (with English language translation).
Combined Office Action and Search Report dated Feb. 29, 2016 in Chinese Patent Application No. 201180058213.4 (with English language translation).
Office Action dated Sep. 30, 2015 in Japanese Patent Application No. 2013-541359 (with English translation).

\* cited by examiner

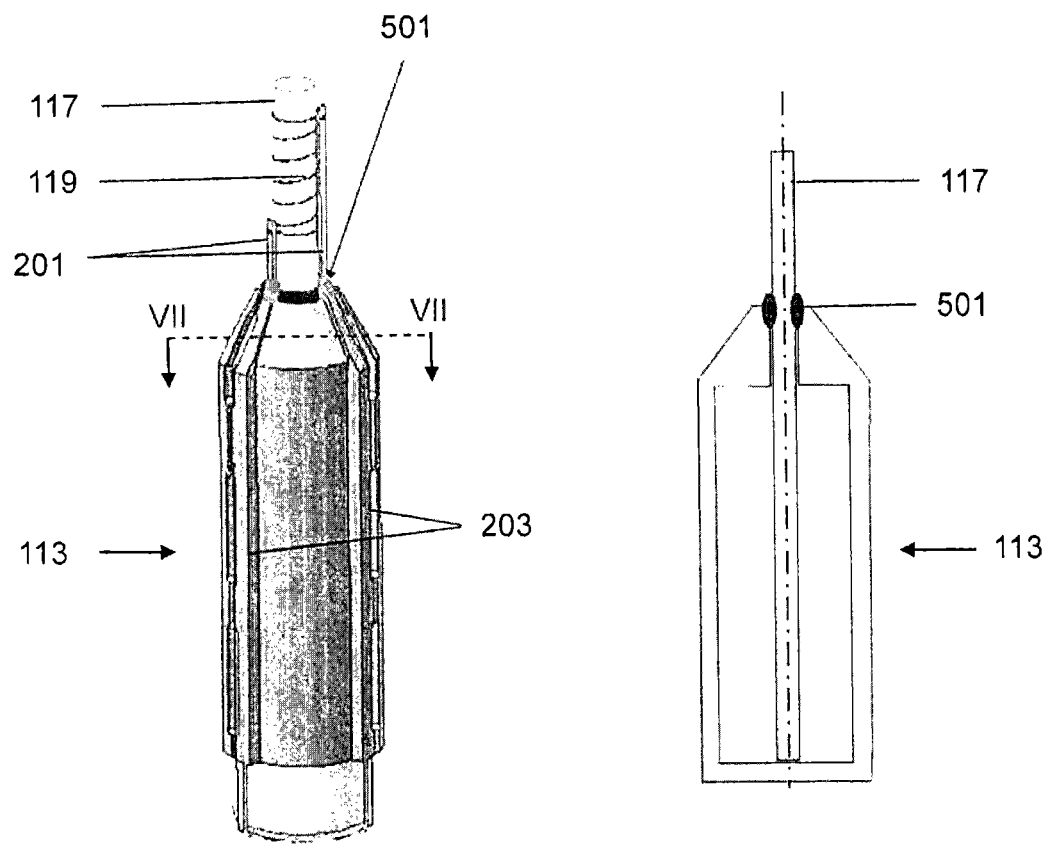
Figure 5
Figure 6
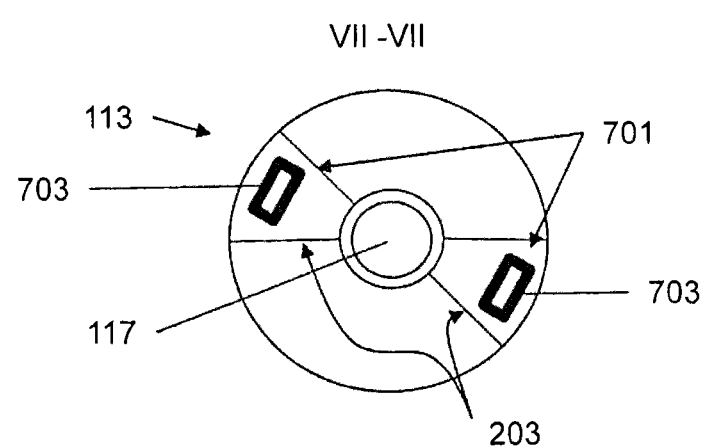
Figure 7

AEROSOL GENERATING SYSTEM WITH LEAKAGE PREVENTION

CROSS REFERENCE TO RELATED APPLICATION

This application is a national phase application based on PCT/EP2011/071553, filed Dec. 1, 2011.

The present invention relates to an aerosol generating system. In particular, the present invention relates to an aerosol generating system in which the aerosol-forming substrate is liquid.

WO-A-2009/132793 discloses an electrically heated smoking system. A liquid is stored in a liquid storage portion, and a capillary wick has a first end which extends into the liquid storage portion for contact with the liquid therein, and a second end which extends out of the liquid storage portion. A heating element heats the second end of the capillary wick. The heating element is in the form of a spirally wound electric heating element in electrical connection with a power supply, and surrounding the second end of the capillary wick. In use, the heating element may be activated by the user to switch on the power supply. Suction on a mouthpiece by the user causes air to be drawn into the electrically heated smoking system over the capillary wick and heating element and subsequently into the mouth of the user.

The aerosol generating systems of the prior art, including the electrically operated smoking system referred to above, do have a number of advantages, but there is still opportunity for improvement in the design.

According to a first aspect of the invention, there is provided an aerosol generating system for heating a liquid aerosol-forming substrate, the system comprising: a liquid storage portion for storing the liquid aerosol-forming substrate; and leakage prevention means configured to prevent or reduce leakage of the liquid aerosol-forming substrate from the liquid storage portion.

The aerosol generating system is arranged to vaporize the aerosol-forming substrate to form the aerosol. The aerosol generating system may include the aerosol-forming substrate or may be adapted to receive the aerosol-forming substrate. As known to those skilled in the art, an aerosol is a suspension of solid particles or liquid droplets in a gas, such as air.

An advantage of the invention is that leakage of liquid from the liquid storage portion is prevented or at least substantially reduced. Minimising, or preferably preventing, leakage is important to avoid wastage of the liquid aerosol-forming substrate. Moreover, leakage of the liquid aerosol-forming substrate may create contamination, for example when different aerosol-forming substrates are used consecutively. In addition, liquid aerosol-forming substrate that has leaked out of the liquid storage portion may flow out of the aerosol generating system and cause inconvenience for the user. For example, the aerosol generating system may become wet or sticky.

The liquid aerosol-forming substrate preferably has physical properties, for example boiling point and vapour pressure, suitable for use in the aerosol generating system. If the boiling point is too high, it may not be possible to vaporize the liquid but, if the boiling point is too low, the liquid may vaporize too readily. The liquid preferably comprises a tobacco-containing material comprising volatile tobacco flavour compounds which are released from the liquid upon heating. Alternatively, or in addition, the liquid may comprise a non-tobacco material. The liquid may include water, solvents, ethanol, plant extracts, nicotine solutions and natural or artificial flavours. Preferably, the liquid further comprises an aerosol former. Examples of suitable aerosol formers are glycerine and propylene glycol.

An advantage of providing a liquid storage portion is that the liquid in the liquid storage portion is protected from ambient air (because air cannot generally enter the liquid storage portion) and, in some embodiments light, so that the risk of degradation of the liquid is significantly reduced. Moreover, a high level of hygiene can be maintained. The liquid storage portion may not be refillable. Thus, when the liquid in the liquid storage portion has been used up, the aerosol generating system is replaced. The leakage prevention means prevent contamination when the liquid storage portion is replaced. Alternatively, the liquid storage portion may be refillable. In that case, the aerosol generating system may be replaced after a certain number of refills of the liquid storage portion. Preferably, the liquid storage portion is arranged to hold liquid for a pre-determined number of puffs.

In one embodiment, the leakage prevention means comprises a porous plug at least partially located within the liquid storage portion.

Providing a porous plug at least partially within the liquid storage portion minimises the free liquid. This reduces the likelihood that liquid will leak from the liquid storage portion at all. The porous plug may comprise any suitable material or combination of materials which is able to retain the liquid aerosol-forming substrate, but is also inert with respect to the liquid aerosol-forming substrate. The particular preferred material or materials will depend on the physical properties of the liquid aerosol-forming substrate. Examples of suitable materials are a capillary material, for example a sponge or foam material, ceramic- or graphite-based materials in the form of fibres or sintered powders, a foamed metal or plastics material, a fibrous material, for example made of spinned or extruded fibres, such as cellulose acetate, polyester, or bonded polyolefin, polyethylene, terylene or polypropylene fibres, nylon fibres or ceramic. The porous plug may have any suitable shape. Most preferably, however, the porous plug substantially fills the cavity of the liquid storage portion so as to minimise the free liquid.

The aerosol generating system may further comprise a capillary wick for conveying the liquid aerosol-forming substrate from the liquid storage portion.

Preferably, the capillary wick is arranged to be in contact with liquid in the liquid storage portion. Preferably, the capillary wick extends into the liquid storage portion. In that case, in use, liquid is transferred from the liquid storage portion by capillary action in the capillary wick. In one embodiment, liquid in one end of the capillary wick is vaporized to form a supersaturated vapour. The supersaturated vapour is mixed with and carried in the air flow. During the flow, the vapour condenses to form the aerosol and the aerosol is carried towards the mouth of a user. The liquid aerosol-forming substrate has physical properties, including surface tension and viscosity, which allow the liquid to be transported through the capillary wick by capillary action.

The capillary wick may have a fibrous or spongy structure. The capillary wick preferably comprises a bundle of capillaries. For example, the capillary wick may comprise a plurality of fibres or threads or other fine bore tubes. The fibres or threads may be generally aligned in the longitudinal direction of the aerosol generating system. Alternatively, the capillary wick may comprise sponge-like or foam-like material formed into a rod shape. The rod shape may extend along the longitudinal direction of the aerosol generating system. The structure of the wick forms a plurality of small bores or tubes, through which the liquid can be transported by capillary action. The capillary wick may comprise any suitable material or combination of materials. Examples of suitable materials are capillary materials, for example a sponge or foam material, ceramic- or graphite-based materials in the form of fibres or sintered powders, foamed metal or plastics material, a fibrous material, for example made of spinned or extruded fibres, such as cellulose acetate, polyester, or bonded polyolefin, polyethylene, terylene or polypropylene fibres, nylon fibres or ceramic. The capillary wick may have any suitable capillarity and porosity so as to be used with different liquid physical properties. The liquid has physical properties, including but not limited to viscosity, surface tension, density, thermal conductivity, boiling point and vapour pressure, which allow the liquid to be transported through the capillary device by capillary action. The physical properties of the liquid aerosol-forming substrate may also affect the leakage behaviour.

In a preferred embodiment, the aerosol generating system comprises a porous plug at least partially located within the liquid storage portion and a capillary wick for conveying the liquid aerosol-forming substrate from the liquid storage portion. In that case, the porous plug and capillary wick may comprise the same material or different materials. Preferably, the capillary wick is arranged to extend into the porous plug which is inside the liquid storage portion. Preferably, the capillary wick extends into substantially the centre of the porous plug. The capillary wick and porous plug are preferably in contact, as this provides for good transfer of liquid. The capillary wick and porous plug may be provided as a single integral capillary member, partially located within the liquid storage portion to retain liquid, and partially extending out of the liquid storage portion to convey the liquid aerosol-forming substrate by capillary action. Alternatively, the capillary wick and porous plug may be separate.

If the aerosol generating system comprises a capillary wick, the leakage prevention means may comprise sealing means between the liquid storage portion and the capillary wick. Such sealing means, particularly in combination with a porous plug, provide improved leakage prevention.

In one embodiment, the sealing means comprises sealing material substantially surrounding the capillary wick. Preferably, the capillary wick is located partially inside the liquid storage portion for contact with the liquid in the liquid storage portion. In that case, preferably, the sealing means comprises sealing material at the junction between the liquid storage portion and the capillary wick. The sealing means may be in the form of a sealing ring.

The sealing means may be particularly important if a porous plug at least partially located within the liquid storage portion is provided and the capillarity of the porous plug is different from the capillarity of the capillary wick. In that case, a capillarity or capillary strength gradient will form between the porous plug in the liquid storage portion and the capillary wick, which may force liquid to move from the liquid storage portion towards the capillary wick.

In a preferred embodiment, the sealing means is created by placing the wick into an injection mould and injecting an appropriate sealing material around the capillary wick. When the capillary wick is placed in the liquid storage portion, the sealing means is positioned at the junction between the liquid storage portion and the capillary wick.

The sealing means preferably substantially seals any gap between the liquid storage portion and the capillary wick. Thus, if any liquid does begin to leak out of the liquid storage portion, the sealing means will prevent any liquid, or reduce the amount of liquid, which exits the liquid storage portion and capillary wick. If the sealing means is provided in addition to a porous plug, any liquid which does escape the porous plug may be contained by the sealing means.

The sealing means may comprise any suitable sealing material or combination of sealing materials. The material may be the same material or a different material as the material of the liquid storage portion.

Preferably, the aerosol generating system is electrically operated. The electrically operated aerosol generating system may further comprise an electric heater for heating the liquid aerosol-forming substrate.

The electric heater may comprise a single heating element. Alternatively, the electric heater may comprise more than one heating element for example two, or three, or four, or five, or six or more heating elements. The heating element or heating elements may be arranged appropriately so as to most effectively heat the aerosol-forming substrate.

The at least one electric heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Del. 19898, United States of America.

Alternatively, the at least one electric heating element may comprise an infra-red heating element, a photonic source or an inductive heating element.

The at least one electric heating element may take any suitable form. For example, the at least one electric heating element may take the form of a heating blade. Alternatively, the at least one electric heating element may take the form of a casing or substrate having different electro-conductive portions, or an electrically resistive metallic tube. The liquid storage portion may incorporate a disposable heating element. Alternatively, one or more heating needles or rods that run through the liquid aerosol-forming substrate may also be suitable. Alternatively, the at least one electric heating element may be a disk (end) heater or a combination of a disk heater with heating needles or rods. Alternatively, the at least one electric heating element may comprise a flexible sheet of material. Other alternatives include a heating wire or filament, for example a Ni—Cr, platinum, tungsten or alloy wire, or a heating plate. Optionally, the heating element may be deposited in or on a rigid carrier material.

The at least one electric heating element may comprise a heat sink, or heat reservoir comprising a material capable of absorbing and storing heat and subsequently releasing the heat over time to heat the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, metal salt, a mixture of eutectic salts or an alloy.

The heat sink or heat reservoir may be arranged such that it is directly in contact with the liquid aerosol-forming substrate and can transfer the stored heat directly to the substrate. Alternatively, the heat stored in the heat sink or heat reservoir may be transferred to the aerosol-forming substrate by means of a heat conductor, such as a metallic tube.

The at least one heating element may heat the aerosol-forming substrate by means of conduction. The heating element may be at least partially in contact with the substrate. Alternatively, the heat from the heating element may be conducted to the substrate by means of a heat conductive element.

Alternatively, the at least one heating element may transfer heat to the incoming ambient air that is drawn through the aerosol generating system during use, which in turn heats the aerosol-forming substrate by convection. The ambient air may be heated before passing through the aerosol-forming substrate. Alternatively, the ambient air may be first drawn through the liquid substrate and then heated.

In one preferred embodiment, the aerosol generating system comprises an electric heater and a capillary wick. In that embodiment, preferably the capillary wick is arranged to be in contact with liquid in the liquid storage portion. In use, liquid is transferred from the liquid storage portion towards the electric heater by capillary action in the capillary wick. In one embodiment, the capillary wick has a first end and a second end, the first end extending into the liquid storage portion for contact with liquid therein and the electric heater being arranged to heat liquid in the second end. When the heater is activated, the liquid at the second end of the capillary wick is vaporized by the heater to form the supersaturated vapour. The supersaturated vapour is mixed with and carried in the air flow. During the flow, the vapour condenses to form the aerosol and the aerosol is carried towards the mouth of a user.

The liquid storage portion, and optionally the capillary wick and the heater, may be removable from the aerosol generating system as a single component.

The aerosol generating system may further comprise at least one electrical connector for the heater. In that case, the leakage prevention means may comprise sealing means between the liquid storage portion and at least one of the electrical connectors.

In one embodiment, the sealing means comprises sealing material substantially surrounding one or both electrical connectors. The sealing means may be in the form of one or more sealing rings. In one embodiment, the electrical connectors are located on the outside of the liquid storage portion. In that case, preferably, the sealing means comprises sealing material at the contact between the liquid storage portion and the electrical connectors. In a preferred embodiment, the sealing means is created by placing each electrical connector into an injection mould and injecting an appropriate sealing material around the connector.

The sealing means preferably substantially prevents liquid running along the electrical connectors. Thus, if any liquid does begin to leak out of the liquid storage portion, the sealing means will prevent any liquid, or reduce the amount of liquid, which runs into the system. If the sealing means between the liquid storage portion and at least one of the electrical connectors is provided in addition to sealing means between the liquid storage portion and the capillary wick, any liquid which is not contained by the sealing means between the liquid storage portion and the capillary wick may be contained by the sealing means between the liquid storage portion and the electrical connectors. If the sealing means between the liquid storage portion and at least one of the electrical connectors is provided in addition to a porous plug, any liquid which does escape the porous plug may be contained by the sealing means.

The sealing means may comprise any suitable sealing material. The material may be the same material or a different material as the material of the liquid storage portion.

The aerosol generating system may further comprise a vaporizer connected to the liquid storage portion for vaporizing the liquid aerosol-forming substrate, and the leakage prevention means may be configured to prevent or reduce leakage of the liquid aerosol-forming substrate from the liquid storage portion and the vaporizer.

In one preferred embodiment, the vaporizer comprises the capillary wick for conveying the liquid aerosol-forming substrate from the liquid storage portion, the capillary wick having a first end extending into the liquid storage portion and a second end opposite the first end, and the electric heater for heating the liquid aerosol-forming substrate in the second end of the capillary wick. However, the invention is not limited to heater vaporizers but may be used in aerosol generating systems in which the vapour and resulting aerosol is generated by a mechanical vaporizer, for example but not limited to a piezo vaporizer or an atomizer using pressurized liquid.

The aerosol generating system may comprise at least one air inlet. The aerosol generating system may comprise at least one air outlet. The aerosol generating system may comprise an aerosol-forming chamber between the air inlet and air outlet so as to define an air flow route from the air inlet to the air outlet via the aerosol-forming chamber, so as to convey the aerosol to the air outlet and into the mouth of a user. The aerosol-forming chamber simply assists or facilitates the generation of the aerosol.

The aerosol generating system may be electrically operated and may further comprise an electric power supply. The aerosol generating system may further comprise electric circuitry. In one embodiment, the electric circuitry comprises a sensor to detect air flow indicative of a user taking a puff. In that case, preferably, the electric circuitry is arranged to provide an electric current pulse to the electric heater when the sensor senses a user taking a puff. Preferably, the time-period of the electric current pulse is pre-set, depending on the amount of liquid desired to be vaporized. The electric circuitry is preferably programmable for this purpose. Alternatively, the electric circuitry may comprise a manually operable switch for a user to initiate a puff. The time-period of the electric current pulse is preferably pre-set depending on the amount of liquid desired to be vaporized. The electric circuitry is preferably programmable for this purpose.

Preferably, the aerosol generating system comprises a housing. Preferably, the housing is elongate. If the aerosol generating includes a capillary wick, the longitudinal axis of the capillary wick and the longitudinal axis of the housing may be substantially parallel. The housing may comprise a shell and a mouthpiece. In that case, all the components may be contained in either the shell or the mouthpiece. In one embodiment, the housing includes a removable insert comprising the liquid storage portion, the capillary wick and the heater. In that embodiment, those parts of the aerosol generating system may be removable from the housing as a single component. This may be useful for refilling or replacing the liquid storage portion, for example.

The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

In one particularly preferred embodiment, the aerosol generating system further comprises: a first end having a mouthpiece; a second end opposite the first end; an electric power supply and electric circuitry arranged in the second end; a capillary wick for conveying the liquid aerosol-forming substrate from the liquid storage portion, the capillary wick having a first end extending into the liquid storage portion and a second end opposite the first end; and an electric heater, connected to the electric power supply, for heating the liquid aerosol-forming substrate in the second end of the capillary wick; wherein the liquid storage portion, capillary wick and electric heater are arranged in the first end of the aerosol generating system.

Preferably, the aerosol generating system is portable. The aerosol generating system may be a smoking system and may have a size comparable to a conventional cigar or cigarette. The smoking system may have a total length between approximately 30 mm and approximately 150 mm. The smoking system may have an external diameter between approximately 5 mm and approximately 30 mm.

Preferably, the aerosol generating system is an electrically operated smoking system.

According to a second aspect of the invention, there is provided a cartridge for storing a liquid aerosol-forming substrate, for use with an aerosol generating system for heating the liquid aerosol-forming substrate, the cartridge comprising: a container for storing the liquid aerosol-forming substrate; and leakage prevention means configured to prevent or reduce leakage of the liquid aerosol-forming substrate from the container. The cartridge may be used with the aerosol generating system of the first aspect of the invention.

In one embodiment, the leakage prevention means comprises a porous plug at least partially located within the container. The properties of such a porous plug have already been discussed.

The cartridge may further comprise a capillary wick for conveying the liquid aerosol-forming substrate from the container. The properties of such a capillary wick have already been discussed.

If the cartridge comprises a capillary wick, the leakage prevention means may comprise sealing means between the container and the capillary wick. The properties of such sealing means have already been discussed.

The cartridge may further comprise an electric heater for heating the liquid aerosol-forming substrate, the electric heater being connectable to an electric power supply in the aerosol generating system. The properties of such an electric heater have already been discussed.

The cartridge may further comprise at least one electrical connector for the heater. In that case, the leakage prevention means may comprise sealing means between the container and at least one of the electrical connectors. The properties of such sealing means have already been discussed.

The cartridge may further comprise a vaporizer connected to the container for vaporizing the liquid aerosol-forming substrate, and the leakage prevention means may be configured to prevent or reduce leakage of the liquid aerosol-forming substrate from the container and the vaporizer.

In one preferred embodiment, the vaporizer comprises the capillary wick for conveying the liquid aerosol-forming substrate from the container, the capillary wick having a first end extending into the container and a second end opposite the first end, and the electric heater for heating the liquid aerosol-forming substrate in the second end of the capillary wick.

Features described in relation to one aspect of the invention may be applicable to another aspect of the invention.

The invention will be further described, by way of example only, with reference to the accompanying drawings, of which:

FIG. 5 is a perspective view of a liquid storage portion according to another embodiment of the invention;

FIG. 6 is a cross-sectional schematic view of the liquid storage portion of FIG. 5; and FIG. 7 is a schematic cross sectional view of a liquid storage portion, for example along line VII-VII of FIG. 5.

Figure 1:
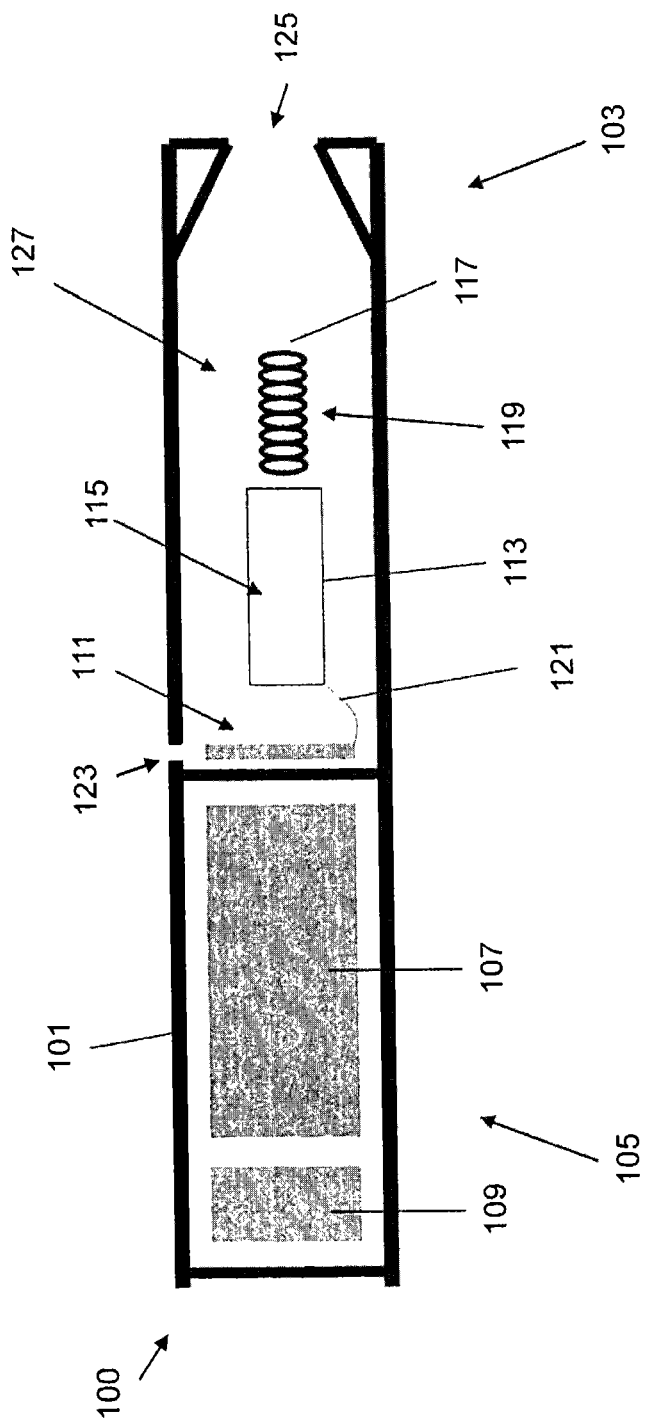
FIG. 1 shows one example of an aerosol generating system having a liquid storage portion.

FIG. 1 shows one example of an aerosol generating system having a liquid storage portion. In FIG. 1, the system is an electrically operated smoking system. The smoking system 100 of FIG. 1 comprises a housing 101 having a first end which is the mouthpiece end 103 and a second end which is the body end 105. In the body end, there is provided an electric power supply in the form of battery 107 and electric circuitry in the form of hardware 109 and puff detection system 111. In the mouthpiece end, there is provided a liquid storage portion in the form of cartridge 113 containing liquid 115, a capillary wick 117 and a heater 119. Note that the heater is only shown schematically in FIG. 1. In the exemplary embodiment shown in FIG. 1, one end of capillary wick 117 extends into cartridge 113 and the other end of capillary wick 117 is surrounded by the heater 119. The heater is connected to the electric circuitry via connections 121, which may pass along the outside of cartridge 113 (not shown in FIG. 1). The housing 101 also includes an air inlet 123, an air outlet 125 at the mouthpiece end, and an aerosol-forming chamber 127.

In use, operation is as follows. Liquid 115 is conveyed by capillary action from the cartridge 113 from the end of the wick 117 which extends into the cartridge to the other end of the wick which is surrounded by heater 119. When a user draws on the aerosol generating system at the air outlet 125, ambient air is drawn through air inlet 123. In the arrangement shown in FIG. 1, the puff detection system 111 senses the puff and activates the heater 119. The battery 107 supplies electrical energy to the heater 119 to heat the end of the wick 117 surrounded by the heater. The liquid in that end of the wick 117 is vaporized by the heater 119 to create a supersaturated vapour. At the same time, the liquid being vaporized is replaced by further liquid moving along the wick 117 by capillary action. (This is sometimes referred to as "pumping action".) The supersaturated vapour created is mixed with and carried in the air flow from the air inlet 123. In the aerosol-forming chamber 127, the vapour condenses to form an inhalable aerosol, which is carried towards the outlet 125 and into the mouth of the user.

In the embodiment shown in FIG. 1, the hardware 109 and puff detection system 111 are preferably programmable. The hardware 109 and puff detection system 111 can be used to manage the aerosol generating system operation.

FIG. 1 shows one example of an aerosol generating system according to the present invention. Many other examples are possible, however. The aerosol generating system simply needs to include or receive a liquid aerosol-forming substrate contained in a liquid storage portion, and some sort of leakage prevention means (to be described below with reference to FIGS. 2 to 7) configured to prevent or reduce leakage of the liquid aerosol-forming substrate from the liquid storage portion. For example, the system need not be electrically operated. For example, the system need not be a smoking system. In addition, the system may not include a heater, in which case another device may be included to vaporize the liquid aerosol-forming substrate. For example, a puff detection system need not be provided. Instead, the system could operate by manual activation, for example the user operating a switch when a puff is taken. For example, the overall shape and size of the housing could be altered. Moreover, the system may not include a capillary wick. In that case, the system may include another mechanism for delivering liquid for vaporization.

However, in a preferred embodiment, the system does include a capillary wick for conveying the liquid from the liquid storage portion. The capillary wick can be made from a variety of porous or capillary materials and preferably has a known, pre-defined capillarity. Examples include ceramic- or graphite-based materials in the form of fibres or sintered powders. Wicks of different porosities can be used to accommodate different liquid physical properties such as density, viscosity, surface tension and vapour pressure. The wick must be suitable so that the required amount of liquid can be delivered to the heater.

As discussed above, according to the invention, the aerosol generating system includes leakage prevention means configured to prevent or reduce leakage of the liquid aerosol-forming substrate from the liquid storage portion. A number of embodiments of the invention, including the leakage prevention means, will now be described with reference to FIGS. 2 to 7. The embodiments are based on the example shown in FIG. 1, although are applicable to other embodiments of aerosol generating systems. Note that FIG. 1 and the following FIGS. 2 to 7 are schematic in nature. In particular, the components shown are not to scale either individually or relative to one another.

Figure 2:
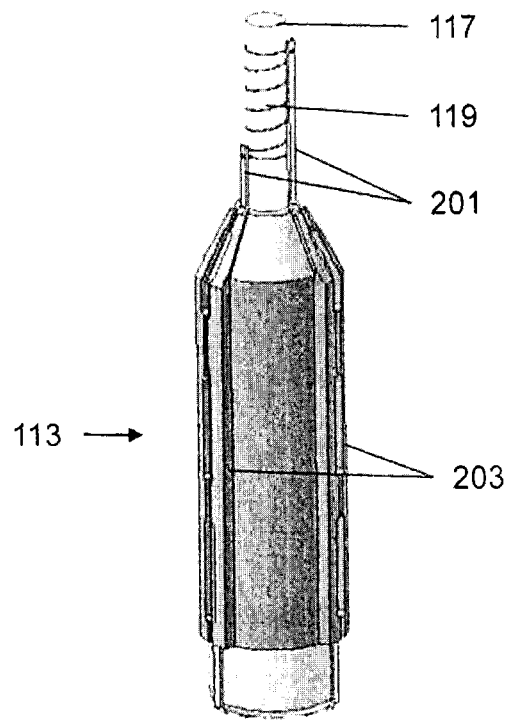
FIG. 2 is a perspective view of a liquid storage portion according to one embodiment of the invention.

FIG. 2 is a perspective view of the liquid storage portion 113, capillary wick 117 and heater 119, for inclusion in an aerosol generating system according to one embodiment of the invention. In FIG. 2, the heater 119 is in the form of a heating coil surrounding and supporting the capillary wick 117. Electrical connection blades 201 connect to each end of the heating coil. The connection blades 201 run along the outside of the liquid storage portion in grooves 203.

Figure 3:
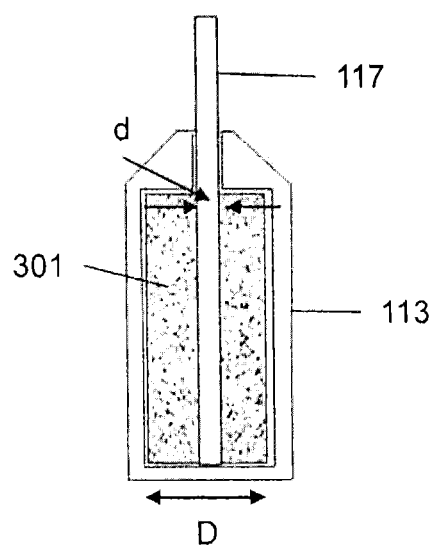
FIG. 3 is a cross-sectional schematic view of the liquid storage portion of FIG. 2.

FIG. 3 is a schematic cross section of the liquid storage portion 113 and capillary wick 117 of FIG. 2. (The heater 119 and electrical connection blades 201 are not shown in FIG. 3 for clarity.) As can be seen in FIG. 3, the liquid storage portion 113 contains a porous plug 301. The porous plug 301 is arranged to hold the liquid in the liquid storage portion 113. In that way, the amount of free liquid, that is to say, liquid which is free to flow, is reduced. Providing such a porous plug reduces the likelihood that liquid will leak from the liquid storage portion. It also improves transfer of liquid to the capillary wick, thereby minimising wastage of liquid, particularly as liquid in the liquid storage portion is used up and the liquid storage portion empties.

The porous plug comprises any material which is suitable for retaining the liquid. Examples of suitable materials are a capillary material, for example a sponge or foam material, a foamed metal or plastics material, a fibrous material, for example made of spinned or extruded fibres, such as cellulose acetate, polyester, or bonded polyolefin, polyethylene, terylene or polypropylene fibres, nylon fibres or ceramic.

Figure 4:
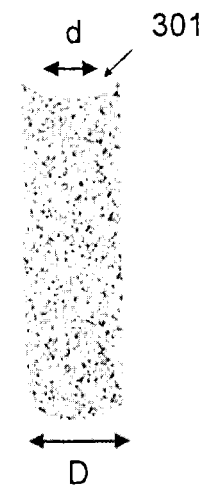
FIG. 4 is a perspective view of the porous plug shown in FIG. 3.

FIG. 4 is a perspective view of a porous plug 301. In this embodiment, the porous plug 301 is in the shape of a cylindrical tube. The outer dimension D of the plug is substantially the same as the inner dimension (not shown) of the liquid storage portion. D is chosen so that the porous plug substantially fills the liquid storage portion. This minimises the amount of free liquid, which may prevent leakage and improve transfer of liquid to the capillary wick. However, the porous plug need not substantially fill the liquid storage portion. For example, the porous plug could be shorter or narrower than the liquid storage portion.

In this embodiment, the inner dimension d of the plug is substantially the same as the diameter of the capillary wick 117, so that the capillary wick 117 may be positioned within the tubular porous plug with a reasonably tight fit. This is advantageous, because the porous plug is then in contact with the capillary wick, which allows for good transfer of liquid from the porous plug to the capillary wick. However, this need not be the case and the inner dimension d of the porous plug may be larger than the diameter of the capillary wick. The capillary wick preferably extends to the bottom of the liquid storage portion, although this need not be the case. Moreover, the porous plug preferably extends to the bottom of the liquid storage portion, although this need not be the case.

Providing a porous plug, as shown in FIGS. 3 and 4, reduces the likelihood of leakage from the liquid storage portion, by absorbing free liquid. That is to say, the amount of liquid which is freely flowing is minimised so that leakage is prevented or at least reduced. In addition, the porous plug may reduce wastage of the liquid because substantially all the liquid, even in the bottom of the liquid storage portion, can be retained by the porous plug and transferred to the capillary wick.

Thus, the porous plug reduces the chance of liquid leakage from the liquid storage portion. However, in the event that liquid aerosol-forming substrate does, nonetheless, leak from the liquid storage portion, further mechanisms for leakage prevention may be provided. These will be described with reference to FIGS. 5, 6 and 7. The leakage prevention means shown in FIGS. 5, 6 and 7 may also be provided separately from a porous plug.

FIG. 5 is a perspective view similar to that of FIG. 2. FIG. 5 is a perspective view of the liquid storage portion 113, capillary wick 117 and heater 119, for inclusion in an aerosol generating system according to a second embodiment of the invention. As in FIG. 2, in FIG. 5, the heater 119 is in the form of a heating coil surrounding and supporting the capillary wick 117. Electrical connection blades 201 connect to each end of the heating coil. The connection blades 201 run along the outside of the liquid storage portion in grooves 203.

FIG. 6 is a schematic cross section of the liquid storage portion 113 and capillary wick 117 of FIG. 5. (The heater 119 and electrical connection blades 201 are not shown in FIG. 6 for clarity.) As can be seen in FIGS. 5 and 6, there is further provided leakage prevention means in the form of seal 501.

In the embodiment illustrated in FIGS. 5 and 6, seal 501 comprises sealing material in the form of a sealing ring 501 at the junction between the liquid storage portion 113 and the capillary wick 117. The sealing ring 501 is a separate solid ring of sealing material (similar to an O-ring) fitting snugly over the capillary wick. In a preferred embodiment, the seal may be created by placing the wick into an injection mould and injecting an appropriate sealing material around the capillary wick. (This is sometimes referred to as "over-moulding".) Then, the capillary wick can then be placed in the liquid storage portion so that the seal is positioned at the junction between the liquid storage portion and the capillary wick.

The sealing ring 501 substantially seals or plugs any gap between the liquid storage portion 113 and the capillary wick 117. Note that the electrical connection blades 201 are preferably located on the outside of the sealing ring 501, as shown in FIG. 5. However, the connection blades 201 could alternatively be located inside the sealing ring 501 or pass directly through the sealing ring 501. Thus, if any liquid does begin to leak out of the liquid storage portion, the sealing ring 501 will prevent the liquid from running into the system and potentially out of the mouthpiece. The sealing ring 501 shown in FIGS. 5 and 6 may be provided in addition to or as an alternative to the porous plug illustrated in FIGS. 2, 3 and 4.

The sealing ring 501 may comprise any suitable sealing material. Preferably, the sealing material is soft, flexible, elastic and liquid-proof. Suitable examples are any elastomer, plastic or rubber. The material of the sealing ring 501 may be the same material as the material of the liquid storage portion 113. Alternatively, the sealing ring 501 may comprise a different material. The sealing ring 501 may further comprise capillary material for retaining any liquid which is collected.

FIG. 7 is a schematic cross sectional view of a liquid storage portion, for example along line VII-VII in FIG. 5. The embodiment shown in FIG. 7 is slightly different from that shown in FIG. 5. FIG. 7 shows the shoulder portion of liquid storage portion 113. The capillary wick 117 is shown positioned in the liquid storage portion 117. The heater 119 and electrical connection blades 201 are not shown for clarity. As in FIG. 5, in FIG. 7, the electrical connection blades run along the outside of the liquid storage portion in grooves 203. However, in the embodiment of FIG. 7, the electrical connection blades extend through apertures 701 in the casing of the liquid storage portion. In FIG. 7, leakage prevention means are provided in the form of seals 703.

Seals 703 comprise sealing material between the liquid storage portion 113 and the electrical connection blades 201. In particular, the electrical connection blades each pass through an aperture in the casing of the liquid storage portion and the sealing material is provided at each aperture, to surround the electrical connection blade passing through the aperture. Seals 703 may be formed in any number of ways. For example, the seals may be applied in liquid form during assembly of the liquid storage portion, capillary wick and heater. Alternatively, the seals may be applied in the form of solid rings of sealing material fitting snugly over each electrical connection blade, before the blades are fixed to the liquid storage portion. Alternatively, the seals may be created by placing each electrical connection blade into an injection mould and injecting an appropriate sealing material around the blade. (This is sometimes referred to as "over-moulding".) Then, the electrical connection blades can be positioned on the liquid storage portion so that the seals are positioned around the apertures.

In the embodiment of FIG. 7, the seals substantially surround the electrical connection blades. It is possible, however, for seals 703 to be provided even if the electrical connection blades do not extend through apertures in the casing of the liquid storage portion. For example, if the electrical connection blades simply run in grooves (for example, as in FIG. 5), sealing material may be provided between the blade and the liquid storage portion. The sealing material may or may not substantially surround the blade.

Thus, if any liquid aerosol-forming substrate does begin to leak out of the liquid storage portion or out of the capillary wick in the region of the heater, and run down the electrical connection blades, seals 703 will prevent the liquid from running into the system and potentially out of the mouthpiece. The seals 703 shown in FIG. 7 may be provided in addition to or as an alternative to the porous plug illustrated in FIGS. 2, 3 and 4 and the sealing ring 501 illustrated in FIGS. 5 and 6. In addition, only one seal need be provided.

Each seal 703 may comprise any suitable sealing material. The material may be the same material as the material of the liquid storage portion 113. Alternatively, the seals 703 may comprise a different material. If sealing ring 501 is also provided, the seals 501 and 703 may comprise the same or different materials. If two seals 703 are provided, the two seals 703 may comprise the same or different materials. The sealing ring 501 may further comprise capillary material for retaining any liquid which is collected. The seals 703 may comprise plastic sheet or film material or composite layers of plastics and metal.

Thus, according to the invention, the aerosol generating system includes leakage prevention means for preventing or at least decreasing leakage of the liquid aerosol-forming substrate from the liquid storage portion. Embodiments of the leakage prevention means have been described with reference to FIGS. 2 to 7. Features described in relation to one embodiment may also be applicable to another embodiment.

The invention claimed is:

1. An electrically-operated aerosol generating system for heating a liquid aerosol-forming substrate, the system comprising:
   a liquid storage portion configured to store the liquid aerosol-forming substrate;
   a capillary wick configured to convey the liquid aerosol-forming substrate from the liquid storage portion;
   an electric heater configured to heat the liquid aerosol-forming substrate;
   at least one electrical connector for the electric heater and being disposed on an outside surface of the liquid storage portion;
   a first seal disposed between the liquid storage portion and the capillary wick and being configured to prevent or reduce leakage of the liquid aerosol-forming substrate from the liquid storage portion, wherein the first seal comprises a sealing ring; and a second seal disposed between the liquid storage portion and the at least one electrical connector, wherein the second seal comprises sealing material substantially surrounding the at least one electrical connector, wherein the liquid storage portion comprises a casing having one or more grooves in its outside surface, and wherein the at least one electrical connector is an electrical connection blade connected to the electric heater and disposed along the outside of the liquid storage portion in the one or more grooves.

2. The aerosol generating system according to claim 1, wherein the first seal further comprises a porous plug at least partially located within the liquid storage portion.

3. The aerosol generating system according to claim 1, wherein the capillary wick is located partially inside the liquid storage portion for contact with the liquid in the liquid storage portion.

4. The aerosol generating system according to claim 3, wherein the sealing ring is positioned at a junction between the liquid storage portion and the capillary wick.

5. The aerosol generating system according to claim 1, further comprising a vaporizer connected to the liquid storage portion and configured to vaporize the liquid aerosol-forming substrate, wherein the first seal is further configured to prevent or reduce leakage of the liquid aerosol-forming substrate from the liquid storage portion and the vaporizer.

6. The aerosol generating system according to claim 1, further comprising:
   a first end having a mouthpiece;
   a second end opposite the first end; and
   an electric power supply and electric circuitry arranged in the second end,
   wherein the capillary wick has a first end extending into the liquid storage portion and a second end opposite the first end,
   wherein the electric heater is connected to the electric power supply and is configured to heat the liquid aerosol-forming substrate in the second end of the capillary wick, and
   wherein the liquid storage portion, the capillary wick, and the electric heater are arranged in the first end of the aerosol generating system.

7. A cartridge for storing a liquid aerosol-forming substrate, for use with an aerosol generating system for heating the liquid aerosol-forming substrate, the cartridge comprising:
   a container configured to store the liquid aerosol-forming substrate;
   a capillary wick configured to convey the liquid aerosol-forming substrate from the container;
   an electric heater configured to heat the liquid aerosol-forming substrate, the electric heater being connectable to an electric power supply in the aerosol generating system;
   at least one electrical connector for the electric heater and being disposed on an outside surface of the container;
   a first seal disposed between the container and the capillary wick and being configured to prevent or reduce leakage of the liquid aerosol-forming substrate from the container, wherein the first seal comprises a sealing ring; and
   a second seal disposed between the container and the at least one electrical connector, wherein the second seal comprises sealing material substantially surrounding the at least one electrical connector,
   wherein the container comprises one or more grooves in its outside surface, and
   wherein the at least one electrical connector electrical connection blade connected to the electric heater and disposed along the outside surface of the container in the one or more grooves.

8. The cartridge according to claim 7, wherein the first seal further comprises a porous plug at least partially located within the container.

9. The cartridge according to claim 7, wherein the capillary wick is located partially inside the container for contact with the liquid in the container.

10. The cartridge according to claim 9, wherein the sealing ring is positioned at a junction between the container and the capillary wick.

11. The cartridge according to claim 7, further comprising a vaporizer connected to the container and configured to vaporize the liquid aerosol-forming substrate, wherein the first seal is further configured to prevent or reduce leakage of the liquid aerosol-forming substrate from the container and the vaporizer.

* * * * *